(12) United States Patent
Jiang et al.

(10) Patent No.: US 7,439,400 B2
(45) Date of Patent: Oct. 21, 2008

(54) AMINO ALCOHOL LIGAND AND ITS USE IN PREPARATION OF CHIRAL PROPARGLIC TERTIARY ALCOHOLS AND TERTIARY AMINES VIA ENANTIOSELECTIVE ADDITION REACTION

(75) Inventors: Biao Jiang, Shanghai (CN); Yugui Si, Shanghai (CN)

(73) Assignee: Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 132 days.

(21) Appl. No.: 10/551,770

(22) PCT Filed: Jun. 16, 2003

(86) PCT No.: PCT/CN03/00462

§ 371 (c)(1),
(2), (4) Date: Oct. 3, 2005

(87) PCT Pub. No.: WO2004/087628

PCT Pub. Date: Oct. 14, 2004

(65) Prior Publication Data

US 2006/0217552 A1    Sep. 28, 2006

(30) Foreign Application Priority Data

Apr. 4, 2003  (CN)  ................. 03 1 16192
May 16, 2003 (CN)  ................. 03 1 17026

(51) Int. Cl.
C07C 33/042 (2006.01)
C07C 29/42 (2006.01)
C07C 215/36 (2006.01)
C07D 239/80 (2006.01)

(52) U.S. Cl. .................. 564/413; 564/341; 564/384; 564/442; 558/488; 556/422

(58) Field of Classification Search ........................ None
See application file for complete search history.

(56) References Cited

U.S. PATENT DOCUMENTS 5,202,484 A      4/1993  Villa et al.
5,932,726 A  *   8/1999  Pierce et al. ................. 544/90

FOREIGN PATENT DOCUMENTS

CN      1314333 A       9/2001
WO      WO 96/37457 A1  11/1996
WO      WO-01/70707     9/2001

WO      WO 01/70707 A2  9/2001

OTHER PUBLICATIONS

Database CAPLUS on STN, Acc. No. 1975:410782, HAJOS, Acta Chimica Academiae Scientiarum Hungaricae (1975), 84(4), p. 471-5 (abstract).*
Database CAPLUS on STN, Acc. No. 1986:19928, Lecavalier et al., Reactive Polymers, Ion Exchangers, Sorbents (1985), 3(4), p. 315-26 (abstract).*
Database CAPLUS on STN, Acc. No. 1990:532763, Lipshutz et al., Journal of the American Chemical Society (1990), 112(19), p. 7032-41 (abstract).*
Database CAPLUS on STN, Acc. No. 1994:435399, Aurich et al., Tetrahedron (1994), 50(13), p. 3929-42 (abstract).*
Database CAPLUS on STN, Acc. No. 1995:1006134, Mastantuono et al., Chirality (1995), 7(7), p. 499-504 (abstract).*
Database CAPLUS on STN, Acc. No. 1995:127344, Fujisawa et al., Chemistry Letters (1994), 10, p. 1777-80 (abstract).*
Database CAPLUS on STN, Acc. No. 1998:728962, Wessig et al., Helvetica Chimica Acta (1998), 81(10), 1803-1814 (abstract).*
Database CAPLUS on STN, Acc. No. 1998:157925, Laieb et al., Journal of Organic Chemistry (1998), 63(5), 1709-1713 (abstract).*
Database CAPLUS on STN, Acc. No. 1999:429251, Chandrasekhar et al., Tetrahedron Letters (1999), 40(27), 5071-5072 (abstract).*
S. Young, A Novel, Highly Potent Non-Nucleoside Inhibitor of the Human Immunodeficiency Virus Type 1 Reverse Transcriptase, Antimicrob. Agents Chemother. vol. 39, No. 12, pp. 2602-2605 (1995).
J. Corbett, Inhibition of Clinically Relevant Mutant Variants of HIV-1 by Quinazolinone Non-Nucleoside Reverse Transcriptase Inhibitors, Journal of Medicinal Chemistry vol. 43, No. 10, 2000, 2019-30.
L. Tan, A Novel, Hightly Enantioselective Ketone Alkynylation Reaction Mediated by Chiral Zinc Aminoalkoxides, Angew. Chem. Int. Ed., No. 5, pp. 711-713 (1999).
M. Pierce, Practical Asymmetric Synthesis of Efavirenz (DMP 266), an HIV-1 Reverse Transcriptase Inhibitor, J. Org. Chem., vol. 63, No. 23, pp. 8536-8543 (1998).
N. Magnis, General Scope of 1,4-Diastereoselective Additions to a 2(3H)-Quinazolinone: Practical Preparation of HIV Therapeutics, J. of Org. Chem., vol. 68, No. 3, pp. 754-761 (2003).
N. Magnus, A New Asymmetric 1,4-addition Method: applicationto the synthesis of the HIV non-nucleoside reverse transcriptase inhibitor DPC 961, Tetrahedron Letters, vol. 41, pp. 3015-3019 (2000).
B. Jiang, Highly Enantioselective Alkynylation of α-Keto Ester: An Efficient Method for Constructing a Chiral Tertiary Carbon Center, Org. Lett., vol. 4, No. 20, pp. 3451-3453 (2002).

* cited by examiner

*Primary Examiner*—Brian J Davis
(74) *Attorney, Agent, or Firm*—Perkins Coie LLP; Manni Li

(57) ABSTRACT

The invention disclosed a new process of asymmetric alkynylation of ketone or ketimine, involving the chiral ligand-mediated asymmetric addition of zinc or copper acetylide to a trifluoromethyl ketone or ketimine intermediate to give a chiral tertiary proparglic alcohols or amines. The adduct compounds include the key precursors to the potent HIV reverse transcriptase inhibitor Efavirenz (DMP 266), DPC 961 and DPC 083. The invention also disclosed a novel chiral amino alcohol ligand.

21 Claims, No Drawings

AMINO ALCOHOL LIGAND AND ITS USE IN PREPARATION OF CHIRAL PROPARGLIC TERTIARY ALCOHOLS AND TERTIARY AMINES VIA ENANTIOSELECTIVE ADDITION REACTION

TECHNICAL FIELD

The present invention relates to a process of asymmetric alkynylation of ketone or ketimine, particularly, the enantioselective addition of terminal alkynes to a trifluoromethyl ketone or ketimine intermediate to give a chiral tertiary proparglic alcohols or amines. The adduct compounds are the key precursors to the potent HIV reverse transcriptase inhibitor Efavirenz (DMP 266), DPC 961, and DPC 083. The present invention also relates to the novel amino alcohol ligand used in the process.

BACKGROUND ART

Human immunodeficiency virus (HIV) is prone to mutation, which leads to drug resistance. It is known that some compounds are reverse transcriptase inhibitors and effective agents in the treatment of HIV and similar diseases, e.g., azidothymidine or AZT. DPC083, DPC 961, and Efavirenz (Sustiva™) are second generation HIV non-nucleoside reverse transcriptase inhibitors (NNRTIs) with enhanced potency. Efavirenz (Sustiva™) has been approved for the treatment of HIV (Antimicrob. Agents Chemother. 1995, 39, 2602). DPC083 and DPC 961 are under clinical evaluation (Journal of Medicinal Chemistry vol. 43, no. 10, 2000, 2019-2030).

Some methods have been reported for the synthesis of Efavirenz (Sustiva™) (Angew. Chem. Int. Ed. no. 5, 1999, 711-713; Journal of Organic Chemistry vol. 63, no. 23, 1998, 8536-8543), DPC083, and DPC 961. These methods disclose the preparation of DPC 961 by a fractional crystallization or 1,4-diastereoselective addition protocol, both employing an auxiliary (Journal of Organic Chemistry vol. 68, no. 3, 2003, 754-761; Tetrahedron Letter vol. 41, 2000, 3015-3019). Very recently, WO0170707 discloses an asymmetric processe for preparing DPC961 via chiral ligand mediated asymmetric addition. However, in the process, a large amount of excess strong base (lithium alkyl and LHMDS) and excess chiral ligand have been used under very strict condition (−20° C.).

SUMMARY OF THE INVENTION

The present invention relates to a new process of asymmetric alkynylation of ketone or ketimine. The invention also provide the new amino alcohol ligand used in the alkynylation process.

A new process of asymmetric alkynylation of ketone or ketimine is disclosed, involving the enantioselective addition of terminal alkynes to a trifluoromethyl ketone or ketimine intermediate to give a chiral tertiary proparglic alcohols or amines. The adduct compounds are the key precursors to the potent HIV reverse transcriptase inhibitor Efavirenz (DMP 266), DPC 961 and DPC 083. This was achieved by direct installation of the quaternary carbon atom of Efavirenz (Sustiva™), DPC083 and DPC 961 with absolute stereo controlling by chiral addition of zinc or copper acetylide to a ketone or ketimine intermediate to give a proparglic alcohol or amine, with enantiomeric excess up to 99%.

Further, it is unexpected that reaction of zinc or copper acetylide with a trifluoromethyl ketone or ketimine produces an optically active product. In the present invention, this is achieved with a new chiral amino alcohol to mediate the addition reaction along an asymmetric pathway. The unusually high levels of optical activity (up to 99% ee) and very mild reaction condition make the method advantageous and practical. The chiral ligand can also be recycled.

The process of the present invention uses an amino alcohol ligand as a catalyst for the asymmetric synthesis of the chiral compound of the structure

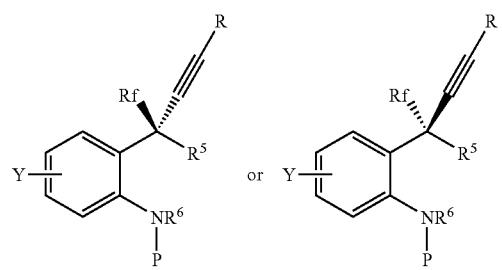

where Y is H mono- or multi-substituted electron-withdrawing group or electron-donating group, preferably, H, mono- or di-subsubstituted electron-withdrawing group or electron-donating group, wherein Y can be located at in-, o-, or p-position of the benzene ring. More preferably, Y is H, Cl, Br, $CH_3SO_2$, $CH_3CH_2SO_2$, $NO_2$, or F. Most preferably, Y is F, Cl, Br. P is hydrogen or an amino protecting group.

Rf is a fluoro-containing alkyl, preferably, a $C_1$~$C_{20}$ fluoro-containing alkyl, and more preferably, a $C_1$~$C_4$ fluoro-containing alkyl.

R is a trialkylsilyl, alkyl, cycloalkyl or aryl group.

$R^6$ is hydrogen when $R^5$ is hydroxyl of the structure:

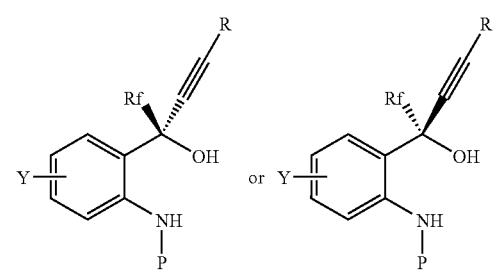

Also, $R^5$ and $R^6$ can be cyclization such as —HNCO— of the structure

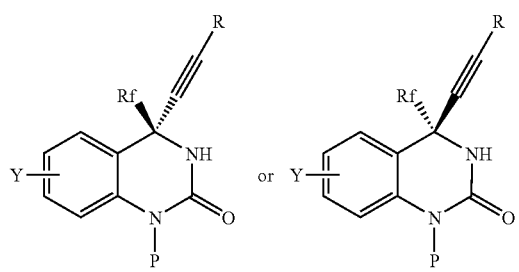

where Y, P, R, Rf is the same as above.

The above amino alcohol ligand is of the structure

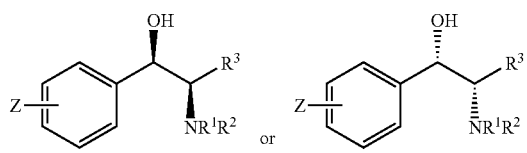

or wherein R¹, R² is amino protecting group, R¹, R² is the same or different group, R³ is alkyl, substituted alkyl (substituted group can be alkyloxy or silyoxy, especially), carboxylic group, carbalkoxy group, hydroxy methyl, cycloalkyl, aryl or $CH_2OR^4$; wherein R⁴ is an oxygen protecting group, Z is H, mono or multisubstituted electronwithdrawing group or electron-donating group, preferred is H, mono or disubsubstituted electronwithdrawing group or electron-donating group, wherein Z can be located at m-, o-, or p-positon of the benzene ring; More preferable is H, F, Cl, Br, I, $CH_3SO_2OH$, $PhCH_2O$, AcO, MeO, EtO, $Me_2NCH_2CH_2O$, $Et_2NCH_2CH_2O$, $PhCH_2OCO$, t-Bu, i-Pr, $NH_2$, or $NO_2$;

The process comprises the steps of:

(a) providing a mixture of chiral ligand (1R,2R)-2-N,N-substituted-1-(substituted-phenyl)-2-R³-substituted-2-aminoethanol or its enantiomer, of the structure

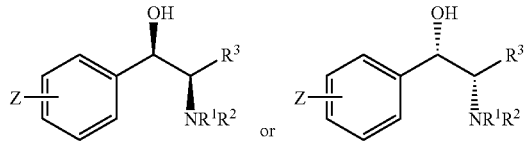

or wherein R¹, R², R³, Z is the same as above;

with a terminal alkyne and a Zn(II), Cu(II) or Cu(I) salts in the presence of an organic base in organic solvent, wherein the terminal alkyne is

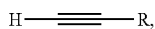

R is the same as above.

(b) mixing with the mixture of step (a) of reactant of the structure

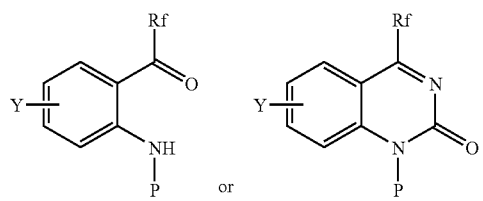

wherein P, Rf, Y is the same as above;

In a preferred embodiment, the above reaction is quenched by adding a proton source to give the desired compound. Preferably, the proton source is a saturated aqueous solution of $NH_4Cl$, water, aqueous hydrochloric acid or citric acid.

In an embodiment, the amino alcohol ligand is a compound of the structure

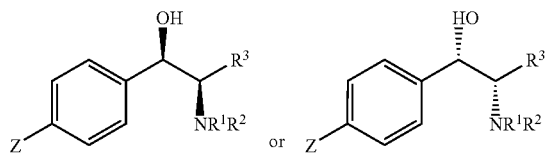

wherein R¹, R², R³, Z is the same as above.

In another embodiment, the chiral ligand is a compound of the structure or its enatiomer

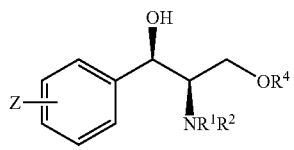

wherein R¹, R², R⁴, Z is the same as above.

In another embodiment, the chiral ligand is a compound of the structure or its enatiomer

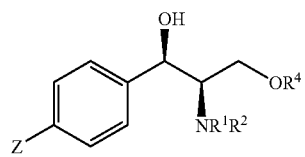

wherein R¹, R², R⁴, Z is the same as above.

In an embodiment, this invention provides a novel process for making a compound of the structure or its enatiomer

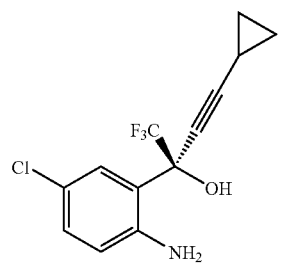

or of the structure or its enatiomer

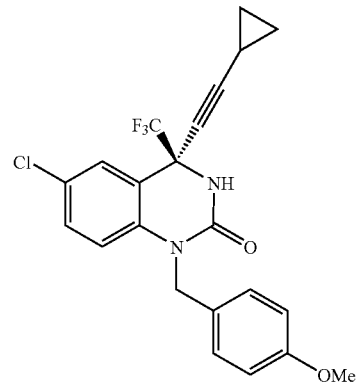

Comprising the steps of:

(a) providing a mixture of 0.1~3 molar equivalent of a chiral ligand (1R,2R)-2-N,N-substitutedamino-1-(4-substituted-phenyl)-3-O-substituted-propane-1-ol, of the structure or its enatiomer,

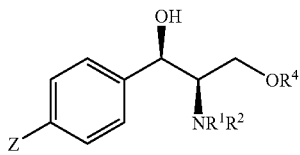

wherein Z, $R^1$, $R^2$, $R^4$ is the same as above,
with 0.1~3 molar equivalent of a terminal alkyne and 0.1~3 molar equivalent of Zn(II), Cu(I) or Cu(II) salts in the presence of 1~4 molar equivalent of an organic base in organic solvent, the terminal alkyne is

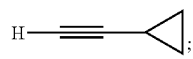

(b) mixing with the mixture of step (a) of 1.0 molar equivalent of reactant of the structure

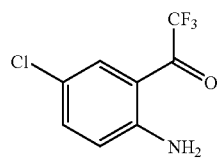

or of the structure that is the 4-methoxybenzyl protected ketimine(I):

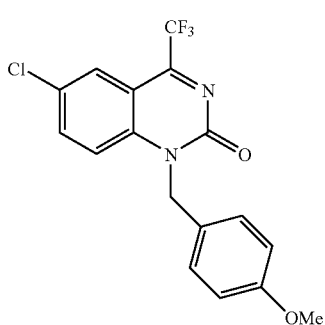

(I)

preferably, maintaining the resulting reaction mixture at a temperature of between about 0-50° C., especially at room temperature for 1-20 hr; quenching by adding a proton source to give the desired compound.

In another embodiment, the chiral ligand is a compound of the structure or its enatiomer

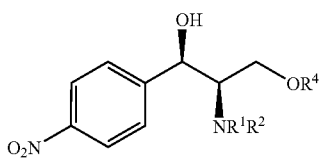

wherein $R^1$, $R^2$, $R^4$ is the same as above; preferrably, $R^1$, $R^2$ is Me.

In another preferred embodiment, the chiral ligand is a compound of the structure or its enatiomer

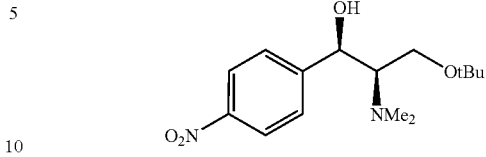

In another preferred embodiment, the chiral ligand is a compound of the structure or its enatiomer

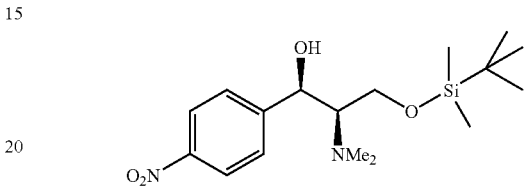

In another preferred embodiment, the chiral ligand is a compound of the structure or its enatiomer

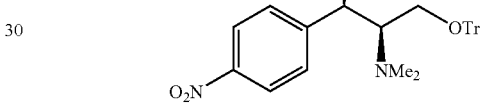

In another embodiment, wherein the stoichiometric ratios are about 0.1-3 equivalent molar of ligand to substrate ketone or ketimine.

In another embodiment, wherein the stoichiometric ratios are about 0.5-3 equivalent molar of ligand to substrate ketone or ketimine.

In another preferred embodiment, wherein the stoichiometric ratios are about 1.2-1.5 equivalent molar of ligand to substrate ketone or ketimine.

In another embodiment, wherein the stoichiometric ratios are about 0.1-3 equivalent molar of terminal alkyne to substrate ketone or ketimine.

In another embodiment, wherein the stoichiometric ratios are about 0.5-3 equivalent molar of terminal alkyne to substrate ketone or ketimine.

In another preferred embodiment, wherein the stoichiometric ratios are about 1.2-1.5 equivalent molar of terminal alkyne to substrate ketone or ketimine.

In another embodiment, the metal salts is selected from $ZnCl_2$, $ZnBr_2$, $ZnF_2$, $ZnI_2$, $Zn(OTf)_2$, $Zn(SO_3CF_2H)_2$, $CuCl_2$, $CuBr_2$, $Cu(OTf)_2$, $CuCl$, $CuBr$, $Cu(OTf)$, $CuI$.

In another preferred embodiment, the Zinc(II) or Cu(II) salts is $Zn(OTf)_2$ or $Cu(OTf)_2$.

In another preferred embodiment, the Zinc(II) is $Zn(OTf)_2$.

In another embodiment, wherein the stoichiometric ratios are about 0.1-3 equivalent molar of the Zinc(II) salt or Cu salt to substrate ketone or ketimine.

In another embodiment, wherein the stoichiometric ratios are about 0.5-3 equivalent molar of the Zinc(II) salt or Cu salt to substrate ketone or ketimine.

In another preferred embodiment, wherein the stoichiometric ratios are about 1.2-1.5 equivalent molar of the Zinc salt or Cu salt to substrate ketone or ketimine.

In another embodiment, wherein the stoichiometric ratios are about 1.0-4.0 equivalent molar of the organic base to substrate ketone or ketimine.

In another embodiment, wherein the stoichiometric ratios are about 2.0~3.5 equivalent molar of the organic base to substrate ketone or ketimine.

In another embodiment, wherein the organic base is selected from MeN(iPr)$_2$, HNEt$_2$, N(iPr)$_3$, pyridine, NEt$_3$, piperidine, NBu$_3$, EtN(iPr)$_2$.

In another preferred embodiment, wherein the organic base is NEt$_3$.

In another embodiment, the reaction is carried out in aprotic solvent or ethereal solvent. Examples of aprotic solvent include THF, dioxane, CH$_2$Cl$_2$ Et$_2$O, benzene, DME, toluene, n-hexane, and cyclohexane, or mixture thereof.

In another preferred embodiment, solvent is toluene.

In another embodiment, wherein the reaction temperature is between about 0° C. and about 100° C.

In another preferred embodiment, wherein the reaction temperature is between about 0° C. and about 50° C., especially at room temperature.

In another embodiment, wherein R$^1$ and R$^2$ is alkyl, substituted alkyl, benzyl or substituted benzyl or trialkysily protected groups, the substituted group can be phenyl, naphenyl, halo, nitro, hydroxy, C$_1$~C$_3$ hydroxy alkyl, C$_1$~C$_4$ alkyl, C$_1$~C$_3$ alkoxy, CN; or R$^1$, R$^2$ can be —(CH$_2$)$_n$X(CH$_2$)$_m$—, where X can be CH$_2$, O or NH; n,m is an integer from 1 to 6.

P is hydrogen, alkyl, substituted alkyl, benzyl or substituted benzyl or trialkylsilyl protected groups, the substituted group can be phenyl, naphenyl, halo, nitro, hydroxy, C$_1$~C$_3$ hydroxyalkyl, C$_1$~C$_4$ alkyl, C$_1$~C$_3$ alkoxy, CN;

R$^4$ is alkyl, substituted alkyl, benzyl or substituted benzyl or trialkylsilyl, the substituted group can be phenyl, naphenyl, halo, nitro, hydroxy, C$_1$~C$_3$ hydroxy alkyl, C$_1$~C$_4$ alkyl, C$_1$~C$_3$ alkoxy, CN;

electronwithdrawing group is halogen, NO$_2$, CF$_3$, CH$_3$S$_2$, CH$_3$CH$_2$SO$_2$, PhCH$_2$OCO, or AcO. electron-donating group is alkoxy (especially C$_1$~C$_3$ alkoxy), OH, Me$_2$NCH$_2$CH$_2$O, Et$_2$NCH$_2$CH$_2$O, NH$_2$, alkyl (especially C$_1$~C$_4$ alkyl).

In another preferred embodiment, wherein R$^1$ and R$^2$ is C$_1$~C$_{20}$ alkyl, C$_1$~C$_{20}$ substituted alkyl, benzyl, substituted benzyl or C$_1$~C$_{20}$ trialkylsilyl protected groups, the substituted group is the same as above; or R$^1$, R$^2$ can be —(CH$_2$)$_n$X(CH$_2$)$_m$—, where X can be CH$_2$, O or NH; n,m is an integer from 1 to 6.

P is hydrogen, C$_1$~C$_{20}$ alkyl, C$_1$~C$_{20}$ substituted alkyl, benzyl or substituted benzyl or C$_1$~C$_{20}$ trialkylsilyl protected groups, the substituted group is the same as above;

R is C$_1$~C$_{20}$ trialkylsilyl, C$_1$~C$_{20}$ alkyl, C$_3$~C$_{20}$ cycloalkyl or aryl, the aryl is phene, naphthalene, furan, thiophene, pyrrole.

R$^3$ is C$_1$~C$_{20}$ alkyl; C$_1$~C$_{20}$ alkyl substituted with alkyloxy or silyoxy, carboxylic group, C$_1$~C$_{20}$ carbalkoxy group, hydroxyl methyl, C$_3$~C$_{20}$ cycloalkyl, aryl or CH$_2$OR$^4$, wherein R$^4$ is C$_1$~C$_{20}$ alkyl, C$_1$~C$_{20}$ substituted alkyl, benzyl or substituted benzyl or C$_1$~C$_{20}$ trialkylsilyl, the substituted group is the same as above.

Z is H, F, Cl, Br, I, CH$_3$SO$_2$OH, PhCH$_2$O, AcO, MeO, EtO, Me$_2$NCH$_2$CH$_2$O, Et$_2$NCH$_2$CH$_2$O, PhCH$_2$OCO, t-Bu, i-Pr, NH$_2$, or NO$_2$;

Y is H, F, Cl, Br, I, CH$_3$SO$_2$OH, PhCH$_2$O, AcO, MeO, EtO, Me$_2$NCH$_2$CH$_2$O, Et$_2$NCH$_2$CH$_2$O, PhCH$_2$OCO, t-Bu, i-Pr, NH$_2$, or NO$_2$;

In another preferred embodiment, wherein R$^1$ and R$^2$ is C$_1$~C$_4$ alkyl, tri-phenyl methyl, t-butyldimethylsilyl, benzyl unsubstituted or substituted with C$_1$~C$_4$ alkyl; para-methoxy benzyl; para-nitrobenzyl; para-chlorobenzyl; 2,4-dichlorobenzyl; 2,4-dimethoxybenzyl; or N-trialkylsilyl groups; or R$^1$, R$^2$ can be —(CH$_2$)$_2$O(CH$_2$)$_2$—, —(CH$_2$)$_2$N(CH$_2$)$_2$—, —(CH$_2$)$_5$— or —(CH$_2$)$_6$—.

P is hydrogen, C$_1$~C$_4$ alkyl, tri-phenyl methyl, t-butyldimethylsilyl, benzyl unsubstituted or substituted with C$_1$~C$_4$ alkyl; para-methoxy benzyl; para-nitrobenzyl; para-chlorobenzyl; 2,4-dichlorobenzyl; 2,4-dimethoxybenzyl;

R is C$_1$~C$_4$ alkyl, C$_3$~C$_6$ cycloalkyl or aryl, the aryl is phene, naphthalene, furan, thiophene, pyrrole.

R$^3$ is C$_1$~C$_4$ alkyl; C$_1$~C$_4$ alkyl substituted with alkyloxy or silyoxy, carboxylic group, C$_1$~C$_4$ carbalkoxy group, hydroxyl methyl, C$_3$~C$_6$ cycloalkyl, aryl or CH$_2$OR$^4$, wherein R$^4$ is C$_1$~C$_4$ alkyl, tri-phenyl methyl, t-butyldimethylsilyl, benzyl unsubstituted or substituted with C$_1$~C$_4$ alkyl; para-methoxy benzyl; para-nitrobenzyl; para-chlorobenzyl; 2,4-dichlorobenzyl; 2,4-dimethoxybenzyl;

Y is H, Cl, Br, CH$_3$SO$_2$, CH$_3$CH$_2$SO$_2$, NO$_2$ or F;

Halogen or halo is fluoro, chloro, bromo and iodo.

The present invention provides a novel chiral ligand or its enatiomer having the structure as follows:

wherein R$^1$, R$^2$ is amino protecting group, R$^1$, R$^2$ is the same or different group, R$^4$ is oxygen protecting group, Z is mono or multisubstituted electronwithdrawing group or electron-donating group, wherein Z can be located at m-, o-, or p-positon of the benzene ring.

Preferably, R$^1$ and R$^2$ is alkyl, substituted alkyl, benzyl, substituted benzyl, or trialkylsilyl group; or R$^1$, R$^2$ can be —(CH$_2$)$_n$X(CH$_2$)$_m$—, where X can be CH$_2$, O or NH; n, m is an integer from 1 to 6.

R$^4$ is alkyl, substituted alkyl, benzyl, substituted benzyl, or trialkylsilyl group; Example of the substituted group of alkyl or benzyl is phenyl, naphthyl, halogen, hydroxy, NO$_2$, C$_1$~C$_3$ alkoxy, CN;

Z is halogen, NO$_2$, CF$_3$, CH$_3$SO$_2$, CH$_3$CH$_2$SO$_2$, CH$_3$O, OH or alkyl;

Preferably, Z is mono or multisubstituted electronwithdrawing group or electron-donating group, more preferably Z is F, Cl, Br, I, CH$_3$SO$_2$OH, PhCH$_2$O, AcO, MeO, EtO, Me$_2$NCH$_2$CH$_2$O, Et$_2$NCH$_2$CH$_2$O, PhCH$_2$OCO, t-Bu, i-Pr, NH$_2$, or NO$_2$ More preferably, R$^1$, R$^2$ is C$_1$~C$_{20}$ alkyl, C$_1$-C$_{20}$ substituted alkyl, benzyl, substituted benzyl, C$_1$-C$_{20}$ trialkylsilyl group; or R$^1$, R$^2$ can be —(CH$_2$)$_n$X(CH$_2$)$_m$—, where X can be CH$_2$, O or NH; n,m is an integer from 1 to 6.

R$^4$ is C$_1$-C$_{20}$ alkyl, C$_1$-C$_{20}$ substituted alkyl, benzyl, substituted benzyl, or C$_1$-C$_{20}$ trialkylsilyl group;

Most Preferably, R$^1$, R$^2$ is C$_1$-C$_4$ alkyl(such as methyl), benzyl unsubstituted or substituted with C$_1$-C$_4$ alkyl; para-methoxy benzyl; para-nitrobenzyl; para-chlorobenzyl; 2,4-dichlorobenzyl; 2,4-dimethoxybenzyl; or trialkylsilyl group; or R$^1$, R$^2$ can be —(CH$_2$)$_2$O(CH$_2$)$_2$—, —(CH$_2$)$_2$N(CH$_2$)$_2$—, —(CH$_2$)$_5$— or —(CH$_2$)$_6$—.

R$^4$ is C$_1$-C$_4$ alkyl (such as butyl), benzyl unsubstituted or substituted with C$_1$-C$_4$ alkyl; para-methoxy benzyl; para-nitrobenzyl; para-chlorobenzyl; 2,4-dichlorobenzyl; 2,4-dimethoxybenzyl; or trialkylsilyl group which exclude t-Butyldimethylsilyl.

Z is Cl, Br, $NO_2$, $CF_3$, $CH_3SO_2$, $CH_3CH_2SO_2$, $CH_3O$, OH or $C_1$~$C_4$ alkyl, especially Z is $CH_3SO_2$ or $NO_2$;

and when Z is $NO_2$ at 4-postion of the phenyl, $R^1$ is N=O, $R^2$ is $COCH_3$, $R^4$ is only alkyl, substituted alkyl, benzyl substituted benzyl, or trialkylsilyl;

and when Z is $NO_2$ at 4-postion of the phenyl, $R^1$, $R^2$ is $CH_3$, the ligand is only (1R,2R)-2-N,N-dimethylamino-1-(4-nitrophenyl)-3-O—$R^4$-1-ol;

and when Z is $OCH_3$ at 4-postion of the phenyl, $R^1$, $R^2$ is $CH_3$, $R^4$ is only alkyl, substituted alkyl, benzyl substituted benzyl; said substituted group is the same as above;

In another embodiment, the novel chiral ligand is a compound of the structure or its enatiomer

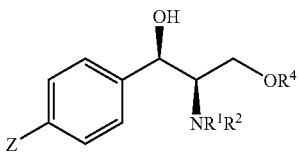

$R^1$, $R^2$, $R^4$, Z is the same as above.

In another embodiment, the novel chiral ligand is a compound of the structure or its enatiomer

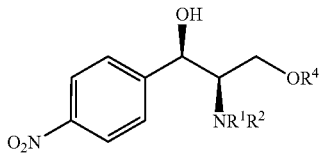

$R^1$, $R^2$, $R^4$ is the same as above, preferably, $R^1$, $R^2$ is Me.

In another preferred embodiment, the novel chiral ligand is a compound of the structure or its enatiomer

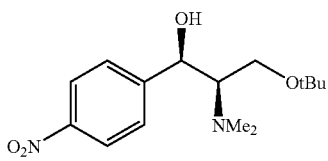

In another preferred embodiment, the novel chiral ligand is a compound of the structure or its enatiomer

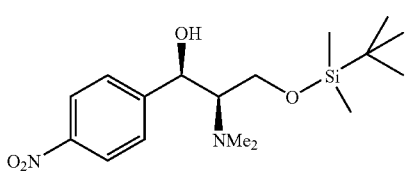

In another preferred embodiment, the novel chiral ligand is a compound of the structure or its enatiomer

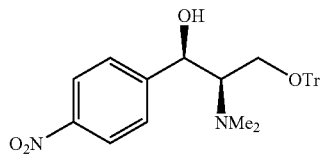

As used herein except where noted, "alkyl" is intended to include both branched- and straight-chain saturated aliphatic hydrocarbon groups having the specified number of carbon atoms; if the number of carbon atoms is unspecified, "alkyl" is intended to include 1 to 20 carbon atoms, preferred is 1 to 4 carbon atoms, both branched and straight-chain saturated aliphatic hydrocarbon groups. For example, methyl, ethyl, propyl, i-propyl, n-butyl, i-butyl, t-butyl.

"Halogen" or "halo" as used herein, means fluoro, chloro, bromo and iodo.

"alkoxyl" is intended to include both branched- and straight-chain groups having the specified number of carbon atoms; if the number of carbon atoms is unspecified, "alkoxyl" is intended to include 1 to 20 carbon atoms, preferred is 1 to 4 carbon atoms.

If the number of carbon atoms is unspecified, "cycloalkyl" is intended to include 3 to 20 carbon atoms, preferred is 3 to 6 carbon atoms.

"aryl" is intended to include phenyl, naphenyl, furan, thiophene, pyrrole, preferred is phenyl.

"carbalkoxy group" is intended to include 1 to 20 carbon atoms, preferred is 1 to 4 carbon In the processes of this present invention, $R^1$ and $R^2$ is the same or different group. $R^1$ and $R^2$ is any suitable amino protecting group, and includes, but is not limited to, alkyl, substituted alkyl (the substituted group can be phenyl, naphenyl, halo, nitro, hydroxy, $C_1$~$C_3$ hydroxy, alkyl, $C_1$~$C_3$ alkoxy, CN), benzyl, substituted benzyl(the substituted group can be phenyl, naphenyl, halo, nitro, hydroxy, $C_1$~$C_3$ hydroxy, alkyl, $C_1$~$C_3$ alkoxy) or trialkylsilyl, or $R^1$, $R^2$ can be —$(CH_2)_nX(CH_2)_m$—, where X can be $CH_2$, O or NH; n,m is an integer from 1 to 6. Examples of $R^1$ or $R^2$ is $C_1$~$C_4$ alkyl, tri-phenyl methyl, t-butyldimethylsilyl, benzyl unsubstituted or substituted with $C_1$~$C_{20}$ alkyl; para-methoxy benzyl; para-nitrobenzyl; para-chlorobenzyl; 2,4-dichlorobenzyl; 2,4-dimethoxybenzyl; preferred is $C_1$-$C_4$ alkyl, benzyl unsubstituted or substituted with $C_1$-$C_4$ alkyl; para-methoxy benzyl; para-nitrobenzyl; para-chlorobenzyl; 2,4-dichlorobenzyl; 2,4-dimethoxybenzyl; or $R^1$, $R^2$ can be —$(CH_2)_2O(CH_2)_2$—, —$(CH_2)_2N(CH_2)_2$—, —$(CH_2)_5$— or —$(CH_2)_6$—. Other protective groups are according to T. W. Greene et al., Protective groups in Organic Synthesis 3rd Ed. John Wiley 1999, pp. 494-653. A preferable amino protecting group is para-methoxybenzyl.

P is hydrogen or any suitable amino protecting group described as above.

In the processes of this present invention, $R^4$ is any suitable oxygen protecting group, and includes, but is not limited to, alkyl, substituted alkyl, benzyl or substituted benzyl or trialkylsilyl protected groups. Preferred is $C_1$~$C_{20}$ alkyl unsubstituted or substituted, benzyl unsubstituted or substituted, or trialkylsilyl protected groups. The substituted group can be phenyl, naphenyl, halo, nitro, hydroxy, $C_1$~$C_3$ hydroxyalkyl, $C_1$~$C_3$ alkoxy, CN. Examples of $R^3$ is $C_1$~$C_4$ alkyl, tri-phenyl methyl, t-butyldimethylsilyl, benzyl unsubstituted or substituted with $C_1$-$C_4$ alkyl; para-methoxy benzyl; para-nitrobenzyl; para-chlorobenzyl; 2,4-dichlorobenzyl; 2,4-dimethoxybenzyl; or trialkylsilyl groups. Other protective groups are according to T. W. Greene et al., Protective groups in Organic Synthesis 3rd Ed. John Wiley 1999, pp. 17-245. A preferable oxygen protecting group is t-butyl.

In the processes of this present invention, electronwithdrawing group includes, but is not limited to, halogen, $NO_2$, $CF_3$, $CH_3SO_2$, $CH_3CH_2SO_2$, $PhCH_2OCO$ or AcO. Electrondonating group includes, but is not limited to, alkoxy especialy $C_1$~$C_{20}$ alkoxy, OH, $Me_2NCH_2CH_2O$, $Et_2NCH_2CH_2O$, $NH_2$, alkyl.

The synthesis of the chiral ligand

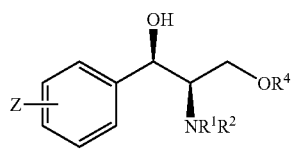

or its enantiomer is based on the simple and short modification of

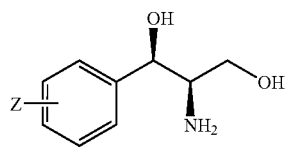

or its enantiomer. The hygroxy group at 3-position and amino at 2-position group was protected according to T. W. Greene et al., Protective groups in Organic Synthesis 3rd Ed. John Wiley 1999.

For example, the amino group at 2-position of

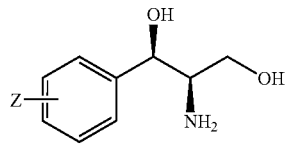

can be protected first by condensation of corresponding aldehyde then by reducing in organic solvent. Example of the reductant can be formic acid, $NaBH_4$, $KBH_4$, $LiAlH_4$ or Pd/C. The amino group at 2-position also can be protected by reaction with $R^1X$ or $R^2X$ in organic solvent in the presence of base, wherein X is halogen. The hygroxy group at 3-position can be protected with t-butyl by reaction with iso-butene catalydzed by acid. The hygroxy group at 3-position also can be protected with $R^3$ by reaction with $R^3X$, wherein X is halogen. The above reaction condition can be routine. Said base can be inorganic base or organic base, for example, $K_2CO_3$, $Na_2CO_3$, NaOH, KOH or $NEt_3$. Example of said organic solvent can be alcohol, alkyl substituted by halogen or ether. Example of the protection detail is refluxing with formaldehyde and formic acid to protect amino group with di-methyl, or reacting with benzaldehyde for condensation and then reducing by NaBH4 to protect the amino group by benzyl group.

Efavirenz, DPC 961 and DPC 083 can be synthesized by the following method.

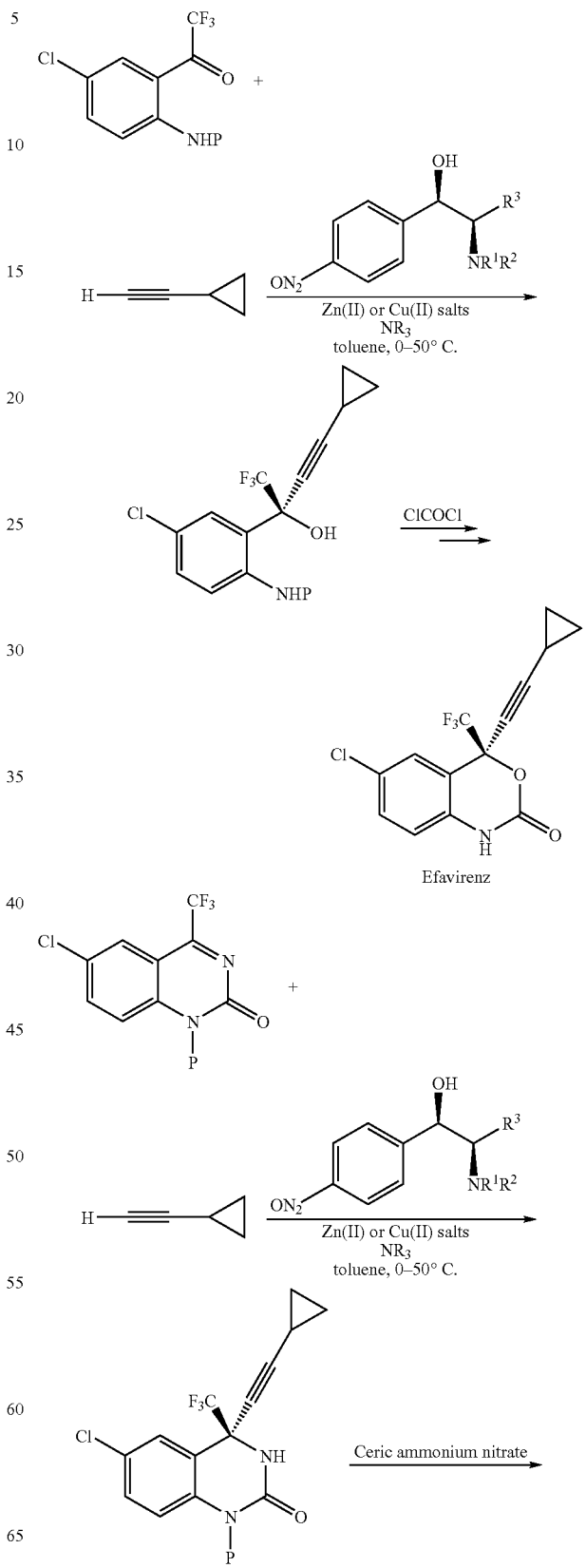

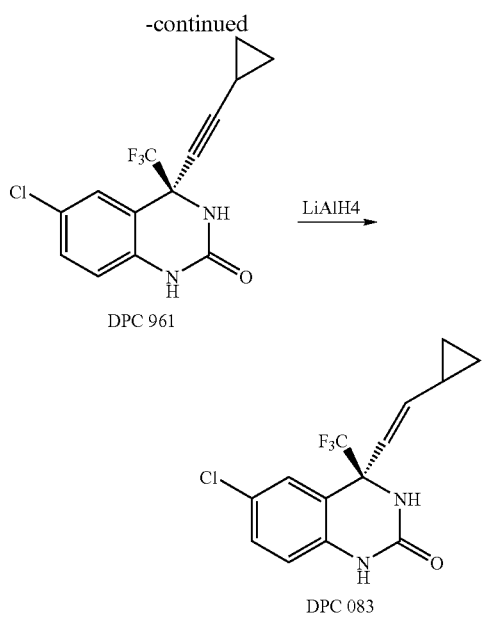

The present invention provides a novel ligand. The use of the ligand relates to asymmetric addition, particularly, a direct synthesis of the optically active DPC 961, DPC083, and efavirenz by chiral addition of zinc or copper acetylide to a ketimine intermediate to give a proparglic amine, with enantiomeric excess up to 99%, or by chiral addition of zinc or copper acetylide to an ketone intermediate to give a proparglic alcohol.

Compared with the prior methods of preparation DPC 961, the process of the present invention provides a chiral amino alcohol to mediate the addition reaction along an asymmetric pathway. The previous methods of derivatization and fractional crystallization or 1,4-diastereoselective addition protocol both employ an auxiliary (*Journal of Organic Chemistry* vol. 68, no. 3, 2003, 754-761; *Tetrahe-dron Letter* vol. 41, 2000, 3015-3019). WO 200170707 discloses an asymmetric process for preparing DPC961 via chiral moderated asymmetric addition. However, the process uses a large amount of excess strong base (lithium alkyl and LHMDS) and excess chiral ligand was-used under very strict condition (−20° C.), while the process of the present invention can be performed with very mild reaction condition (20-40° C.). The ligand used in the reaction of the present invention is less expensive. Furthermore, the ligand in the reaction of the present invention can be recycled. The workup is also very simple. All of the advantages render the reduction of the cost of the process greatly.

Further, it is unexpected that reaction of zinc or copper acetylide with a trifluoromethyl ketimine produces an optically active product. The invention not only provide a kind of novel ligand in the enantioselective alkynylation of ketimine, but also provide a practical industrial process of preparation DPC 961. In the present invention, this is achieved with a chiral amino alcohol to mediate the addition reaction along an asymmetric pathway. The unusually high levels of optical activity (up to 99% ee) and very mild reaction condition make the method advantageous and practical.

DETAILED DESCRIPTION OF THE INVENTION

Other features of the invention will become apparent in the course of the following descriptions of exemplary embodiments that are given for illustration of the invention and are not intended to be limiting thereof.

EXAMPLE 1

Preparation of (1R,2R)-2-N,N-dimethylamino-3-(p-nitrophenyl)propane-1,3-diol

See reference Jiang, B.; Chen, Z. L.; Tang, X. X. *Org. Lett.* 2002, 4, 3451.

EXAMPLE 2

Preparation of (1R,2R)-3-(t-butyloxy)-2-N,N-dimethylamino-1-(p-nitrophenyl)propane-1-ol Concentrated $H_2SO_4$ (0.8 g) was added dropwise to a solution of (1R,2R)-2-N,N-dimethylamino-3-(p-nitrophenyl)propane-1,3-diol (1.8 g, 7.5 mmol) in $CH_2Cl_2$ (20 mL) at 0-5° C. Isobutene gas was bubbled for 1 h with the temperature maintained at 0-5° C. Concentrated $H_2SO_4$ (0.2 g) was added dropwise, the mixture was allowed to warm to room temperature and was stirred vigorously for 5-7 hrs with the isobutene bubbling into. Then the mixture was cooled to 0-5° C. and washed with $K_2CO_3$ (sat). The organic layer was dried with $Na_2SO_4$ and concentrated in vaccuo. Purified by flash chromatography on silica gel afforded the ligand (1.44 g, 65%). (Hexane:EtOAc=1:1). mp 100.0-101.3° C.; $[\alpha]_D^{20}$=+23.5 (c, 1.00, $CHCl_3$); FTIR (KBr) 3333, 2972, 1606, 1523, 1357, 1197, 861 $cm^{-1}$; $^1H$ NMR (300 MHz, $CDCl_3$) δ 8.19 (d, J=8.8 Hz, 2H), 7.60 (d, J=8.4 Hz, 2H), 4.59 (d, J=9.9 Hz, 1H), 3.34 (dd, J=3.0 Hz, and 9.9 Hz, 1H), 3.21 (dd, J=6.5 Hz, and 10 Hz, 1H), 2.56 (m, 1H), 2.47 (s, 6H), 1.06 (s, 9H); $^{13}C$ NMR (75 MHz, $CDCl_3$) δ 150.6, 147.6, 128.46, 123.49, 73.3, 70.3, 69.8, 56.0, 41.8, 27.4; MS (EI) m/e 223(M+−73, 3), 209 (21), 144 (68), 88 (100), 71 (10), 57 (31); Anal. calcd. for $C_{15}H_{24}N_2O_4$: C, 60.81; H, 8.11; N, 9.46. Found: C, 60.72; H, 8.26; N, 9.14.

EXAMPLE 3

Preparation of (1R,2R)-3-(t-butyldimethylsilyloxy)-2-N,N-dimethylamino-1-(p-nitrophenyl)propane-1-ol (1R,2R)-2-N,N-dimethylamino-3-(p-nitrophenyl)propane-1,3-diol (1.946 g, 8.1 mmol) was dissolved in $CH_2Cl_2$ (30 mL), TBDMSCl (1.28 g, 5.3 mmol) and imidazole (1.4 g, 20.6 mmol) was added at 0° C. The mixture was stirred for overnight at rt. Work up to give 2.72 g proguct. FTIR (KBr) 3344, 2954, 1606, 1525, 1349 $cm^{-1}$; $^1H$ NMR (300 MHz, $CDCl_3$) δ 8.25-8.20 (d, J=8.5 Hz, 2H), 7.6-7.55 (d, J=8.5 Hz, 2H), 4.65 (d, J=9.7 Hz, 1H), 3.77-3.6(dd, J=11.3 Hz, 2.7 Hz 1H), 3.5-3.45(dd, J=11.3 Hz, 6.0 Hz, 1H), 2.50 (m, 7H), 1.85 (s, 9H), 0.1 (s, 6H); $^{13}C$ NMR (75 MHz, $CDCl_3$) δ 150.2, 147.4, 128.0, 123.3, 69.0, 57.1, 41.6, 25.7, 17.9, −5.9; MS (EI) m/e 297(M+−57, 0.3), 209 (8.2), 202 (100). Anal. calcd. for $C_{17}H_{30}N_2O_4Si$: C, 57.60; H, 8.53; N, 7.90. Found: C, 57.82; H, 8.18; N, 7.77.

EXAMPLE 4

Preparation of (1R,2R)-3-(triphenylmethoxy)-2-N,N-dimethylamino-1-p-nitrophenyl)propane-1-ol (1R,2R)-2-N,N-dimethylamino-3-p-nitrophenyl)propane-1,3-diol (1.946 g, 8.1 mmol) was dissolved in $CH_2Cl_2$ (50 mL), Triphenylmethane chloride (TrCl) (3.34 g, 12 mmol)

and Et₃N (2 mL) was added at 0° C. The mixture was stirred for overnight at rt. Work up to give 3.7 g proguct. FTIR (KBr) 3344, 2954, 1606, 1525, 1349 cm⁻¹; ¹H NMR (300 MHz, CDCl₃) δ8.09-8.06 (d, J=8.4 Hz, 2H), 7.36-7.33 (d, J=8.6 Hz, 2H), 7.25-7.17 (m, 15H), 4.27 (d, J=10.0 Hz, 1H), 3.28(dd, J=10.2 Hz, 6.4 Hz, 1H), 3.01(dd, J=10.7 Hz, 3.9 Hz, 1H), 2.71 (m, 1H), 2.45 (s, 6H); ¹³C NMR (75 MHz, CDCl₃) δ 150.1, 147.6, 143.6, 128.9, 128.8, 128.7, 128.6, 128.4, 128.1, 127.9, 127.8, 127.3, 123.7, 87.7, 70.9, 70.6, 58.6, 41.6.

EXAMPLE 5

Preparation of (1R,2R)-2-N-benzyl-2-N-methy-lamino-3-p-nitrophenyl)propane-1,3-diol (1R,2R)-2-aminol-3-(p-nitrophenyl)propane-1,3-diol (2.12 g, 10 mmol) and benzaldehyde (1.2 g, 10.5 mmol) was added to methanol (10 mL), then CuSO₄ (0.2 g) was added to the mixture. The mixture was refluxed for 7 hr, cooled to rt and filtered. To the filtrate was added THF (10 mL). NaBH₄ (0.4 g) was added slowly. The resulting mixture was refluxed for 2 hr and cooled. 5% HCl was added to acidified the solution. Extracted with ether and concentrated. The residue mixture was refluxed with HCHO (10 mL) and HCOOH (10 mL) for 8 hr. The mixture was cooled and nutralized with NaOH. Extracted with CH₂Cl₂ and dried with NaSO₄. After purification give 1.2 g product.

EXAMPLE 6

Preparation of (1R,2R)-3-(t-butyldimethylsilyloxy)-2-N-benzyl-2-N-methylamino-1-(p-nitrophenyl)propane-1-ol (1R,2R)-2-N-benzyl-N-methylamino-3-p-nitrophenyl)propane-1,3-diol (632 mg) was dissolved in CH₂Cl₂ (15 mL), TBDMSCl (300 mg, 2 mmol) and imidazole (136 mg, 2 mmol) was added at 0° C. The mixture was stirred for overnight at rt. Work up to give 600 mg proguct. FTIR (KBr) 3344, 2972, 1606, 1525, 1348 cm⁻¹; ¹H NMR (300 MHz, CDCl₃) δ 8.17 (d, J=8.8 Hz, 2H), 7.50 (d, J=8.4 Hz, 2H), 7.38-7.31 (m, 5H), 4.70 (d, J=9.6 Hz, 1H), 4.04 (d, J=13.0 Hz, 1H), 3.77-3.55(m, 3H), 2.70 (m, 1H), 2.43 (s, 3H), 0.90 (s, 9H), 0.01 (s, 6H); ¹³C NMR (75 MHz, CDCl₃) δ 150.6, 147.6, 138.46, 129.2, 128.8, 128.4, 127.7, 123.69, 70.3, 69.8, 60.1, 58.0, 37.5, 26.0, 18.3, −5.4; MS (EI) m/e 415(M+−15, 0.9), 278 (100), 91 (73);

EXAMPLE 7

Preparation of (1R,2R)-3-(triphenylmethoxy)-2-N-benzyl-2-N-methylamino-1-(p-nitrophenyl)propane-1-ol (1R,2R)-2-N-benzyl-N-methylamino-3-(p-nitrophenyl)propane-1,3-diol (380 mg, 1.2 mmol) was dissolved in CH₂Cl₂ (15 mL), TrCl (334 mg, 1.2 mmol) and Et₃N (0.2 mL) was added at 0° C. The mixture was stirred for overnight at rt. Work up to give 500 mg proguct. mp 58.0-59.3° C.; FTIR (KBr) 3314, 2926, 1602, 1521, 1346 cm⁻¹; ¹H NMR (300 MHz, CDCl₃) δ 8.07 (d, J=8.8 Hz, 2H), 7.40-7.19 (m, 22H), 4.30 (d, J=9.6 Hz, 1H), 3.94 (d, J=13.0 Hz, 1H), 3.73(d, J=6.8 Hz, 1H), 3.36 (m, 1H), 3.06 (m, 1H) 2.89 (m, 1H), 2.33 (s, 3H); ¹³C NMR (75 MHz, CDCl₃) δ 150.6, 147.6, 143.46, 138.2, 129.3, 128.8, 128.7, 128.6, 128.4, 128.0, 127.7 127.4, 123.7, 87.8, 70.5, 69.8, 60.1, 58.0, 37.0; MS (EI) m/e 406 (M+−152, 24.9), 243 (100); Anal. calcd. for C₁₅H₂₄N₂O₄: C, 77.42; H, 6.09; N, 5.02. Found: C, 77.26; H, 6.06; N, 4.65.

EXAMPLE 8

Preparation of (1R,2R)-3-(triphenylmethoxy)-2-N,N-dimethylamino-1-(phenyl)propane-1-ol (1R,2R)-2-N,N-dimethylamino-3-(phenyl)propane-1,3-diol (1.95 g, 10 mmol) was dissolved in CH₂Cl₂ (50 mL), Triphenylmethane chloride (TrCl) (3.33 g, 12 mmol) and Et₃N (2 mL) was added at 0° C. The mixture was stirred for overnight at rt. Work up to give 4.0 g proguct. FTIR (KBr) 3344, 2954, 1609, 1525, 1349 cm⁻¹; ¹H NMR (300 MHz, CDCl₃) δ 7.26-7.06 (m, 20H), 4.87 (d, J=10.0 Hz, 1H), 3.76 (dd, J=10.2 Hz, 6.4 Hz 1H), 3.51(dd, J=10.7 Hz, 3.9 Hz 2H), 2.80 (m, 1H), 2.38 (s, 6H); ¹³C NMR (75 MHz, CDCl₃) δ 143.6, 138.9, 128-129 (16 C), 125.7-126.6 (4 C), 84.9, 72.9, 68.6, 69.6, 49.6, 39.6.

EXAMPLE 9

Preparation of (1R,2R)-3-(triphenylmethoxy)-2-N,N-dimethylamino-1-(p-methylsulphonylphenyl)propane-1-ol (1R,2R)-2-N,N-dimethylamino-3-(p-methylsulphonylphenyl)propane-1,3-diol (5.46 g, 20 mmol) was dissolved in CH₂Cl₂ (80 mL), Triphenylmethane chloride (TrCl) (6.8 g, 25 mmol) and Et₃N (4 mL) was added at 0° C. The mixture was stirred for overnight at rt. Work up to give 9.10 g proguct. FTIR (KBr) 3344, 2954, 1609, 1525, 1349 cm⁻¹; ¹H NMR (300 MHz, CDCl₃) δ 7.48-7.40 (d, J=8.4 Hz, 2H), 7.27-7.19 (d, J=8.6 Hz, 2H), 7.12-7.04 (m, 15H), 4.86(d, J=10.0 Hz, 1H), 3.72 (dd, J=10.2 Hz, 6.4 Hz 1H), 3.56(dd, J=10.2 Hz, 6.4 Hz 2H), 2.94(s, 3H), 2.81(m, 1H), 2.38(s, 6H); ¹³C NMR (75 MHz, CDCl₃), δ 143.8, 143.0, 138.6, 135.0, 129-126(16C), 84.9, 72.9, 69.6, 68.0, 49.6, 41.0, 39.6.

EXAMPLE 10

Preparation of (1R,2R)-2-N-prrrolidinyl-3-(p-nitrophenyl)propane-1,3-diol (1R,2R)-2-amino-3-(p-nitrophenyl)propane-1,3-diol (2.12 g, 10 mmol) dissolved in DMF (10 mL), anhydrous K₂CO₃ (3.15 g, 22 mmol) was added at 0-5° C. 1,4-dibromobutane (2.4 g, 11 mmol) was added dropwise. The mixture was allowed to warm to room temperature and was stirred vigorously for 35 h. After filtration, the solution was added to water and extracted with EtOAc. Purified to give the product 2.2 g (83%) as an yellow oil. FTIR (neat) 3393, 2969, 1605, 1521, 1348cm⁻¹; ¹H NMR (300 MHz, CDCl₃) δ 8.10 (d, J=8.9 Hz, 2H), 7.53 (d, J=8.7 Hz, 2H), 4.63 (d, J=8.1 Hz, 1H), 3.80 (br, 2H), 3.56 (m, 2H), 2.81-2.70 (m, 5H), 1.79-1.68 (m, 4H); MS (ESI) m/e 267(M⁺+1).

EXAMPLE 11

Preparation of (1R,2R)-3-(t-butyldimethylsilyloxy)-2-N-prrrolidinyl-1-(p-nitrophenyl)propane-1-ol (1R,2R)-2-N-prrrolidinyl-3-(p-nitrophenyl)propane-1,3-diol (2.66 g, 10 mmol) was dissolved in CH₂Cl₂ (80 mL). After cooled to 0-5° C., imidazole (680 mg, 10 mmol) was added. TBDMSCl (1.65 g 11 mmol) was added in three portions. The mixture was allowed to warm to room temperature and was stirred for 5 h. After workup to give 3.0 g (79%) yellow oil as product. FTIR (neat) 3346, 2937, 2924, 2858, 1604, 1525, 1347cm⁻¹; ¹H NMR (300 MHz, CDCl₃) δ 8.18

(d, J=8.5 Hz, 2H), 7.59 (d, J=8.9 Hz, 2H), 4.70 (d, J=8.5 Hz, 1H), 3.65 (dd, J=4.0 Hz, and 11.0 Hz, 1H), 3.52 (dd, J=5.3 Hz, and 10.8 Hz, 1H), 2.82-2.71 (m, 5H), 1.83-1.73 (m, 4H), 0.85 (s, 9H), −0.08 (s, 6H); $^{13}$C NMR (75 MHz, CDCl$_3$) δ 150.8, 147.2, 127.7, 123.2, 69.8, 67.4, 58.2, 49.2, 25.7, 23.4, 17.9, −5.8; MS (ESI) m/e 381(M$^+$+1).

EXAMPLE 12

Under argon atmosphere, the amino alcohol ligand (1R, 2R)-2-N,N-dimethyl-1-(4-nitrophenyl)-3-O-t-butylpropane-1-ol (2.96 g, 0.2 mmol) and Zn(OTf)$_2$ (3.6 g, 10 mmol) was dissolved in toluene (10 mL) at 25° C. NEt$_3$ (2.1 mL, 15 mmol) was added. After 1 hr, the neat cyclopropylacetylene (1.2 mL, 12 mmol) and 4-chloro-2-trifluoroacetyl aniline (1.74 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with Na$_2$SO$_4$ and concentrated in vacuo. Heptane was added to the mixture slowly. The white solid was collected by filtration, and dried to give the adduct product (75% yield, 99.3% ee).

EXAMPLE 13

Under argon atmosphere, the amino alcohol ligand (1R, 2R)-2-N,N-dimethyl-1-(4-nitrophenyl)-3-O-t-butyldimethylsilylpropane-1-ol (3.54 g, 10 mmol) and Zn(OTf)$_2$ (3.6 g, 10 mol) was dissolved in toluene (10 mL) at 25° C. NEt$_3$ (2.1 mL, 15 mmol) was added. After 1 hr, the neat cyclopropylacetylene (1.2 mL, 12 mmol) was added to the mixture. The mixture was stirred at 25° C. for 2 hr. The 4-chloro-2-trifluoroacetyl aniline (2.23 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with Na$_2$SO$_4$ and concentrated in vacuo. Heptane was added to the mixture slowly. The white solid was collected by filtration, and dried to give the adduct product (60% yield, 90.1% ee).

EXAMPLE 14

Under argon atmosphere, the amino alcohol ligand (1R, 2R)-2-N,N-dimethyl-1-(4-nitrophenyl)-3-O-t-butylpropane-1-ol (2.96 g, 10 mmol) and Zn(OTf)$_2$ (3.6 g, 10 mmol) was dissolved in toluene (10 mL) at 25° C. NEt$_3$ (2.1 mL, 15 mmol) was added. After 1 hr, the neat cyclopropylacetylene (1.2 mL, 12 mmol) was added to the mixture. The mixture was stirred at 25° C. for 2 hr. The 4-chloro-2-trifluoroacetyl aniline (2.23 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with Na$_2$SO$_4$ and concentrated in vacuo. Heptane was added to the mixture slowly. The white solid was collected by filtration, and dried to give the adduct product (60% yield, 99.1% ee).

EXAMPLE 15

Under argon atmosphere, the amino alcohol ligand (1R, 2R)-2-N,N-dimethyl-1-(4-nitrophenyl)-3-O-t-butyldimethylsilylpropane-1-ol (354 mg, 1 mmol) and Zn(OTf)$_2$ (0.36 g, 1 mmol) was dissolved in toluene (2 mL) at 25° C. NEt$_3$ (0.21 mL, 1.5 mmol) was added. After 1 hr, the neat t-butylacetylene (1.3 mL, 12 mmol) was added to the mixture. The 4-chloro-2-trifluoroacetyl aniline (2.3 g, 10 mmol) was added in one port. The mixture was stirred at 25° C. for 10 hr. The resulting solution was quenched by adding 1N HCl aqueous solution. The mixture was extracted with EtOAc. The aqueous was saved for the recovery of ligand. The combined organic layers was dried with Na$_2$SO$_4$ and concentrated in vacuo. Heptane was added to the mixture slowly. The white solid was collected by filtration, and dried to give the adduct product (85% yield, 94.1% ee).

EXAMPLE 16

Under argon atmosphere, the amino alcohol ligand (1R, 2R)-2-N-benzyl-N-methylamino-1-(4-nitrophenyl)-3-O-tritylpropane-1-ol (558 mg, 1 mmol) and Cu(OTf)$_2$ (0.36 g, 1 mmol) was dissolved in toluene (10 mL) at 25° C. NEt$_3$ (0.21 mL, 1.5 mmol) was added. After 1 hr, the neat phenylacetylene (1.1 mL, 10 mmol) was added to the mixture. The 4-chloro-2-trifluoroacetyl aniline (2.3 g, 10 mmol) was added in one port. The mixture was stirred at 25° C. for 10 hr. The resulting solution was quenched by adding citric acid aqueous solution. The mixture was extracted with EtOAc. The aqueous was saved for the recovery of ligand. The combined organic layers was dried with Na$_2$SO$_4$ and concentrated in vacuo. Heptane was added to the mixture slowly. The white solid was collected by filtration, and dried to give the adduct product (67% yield, 55% ee).

EXAMPLE 17

Under argon atmosphere, the amino alcohol ligand (1R, 2R)-2-methyl-2-N-benzyl-N-methylamino-1-phenyl-ethane-1-ol (2.55 g, 10.0 mmol) and Zn(OTf)$_2$ (3.6 g, 10.0 mmol) was dissolved in toluene (10 mL) at 25° C. NEt$_3$ (2.1 mL, 15 mmol) was added. After 1 hr, the neat cyclopropylacetylene (1.2 mL, 12 mmol) was added to the mixture. The mixture was stirred at 25° C. for 2 hr. The 4-chloro-2-trifluoroacetyl aniline (2.23 g, 10 mmol) was added in one port. The mixture was stirred at 25° C. for 10 hr. The resulting solution was quenched by adding NH$_4$Cl aqueous solution. The mixture was extracted with EtOAc. The aqueous was saved for the recovery of ligand. The combined organic layers was dried with Na$_2$SO$_4$ and concentrated in vacuo. Heptane was added to the mixture slowly. The white solid was collected by filtration, and dried to give the adduct product (51% yield, 96.1% ee).

EXAMPLE 18

Under argon atmosphere, the amino alcohol ligand (1R, 2R)-2-N,N-dimethyl-1-(4-nitrophenyl)-3-O-t-butylpropane-1-ol (2.96 g, 10 mmol) and Zn(OTf)$_2$ (3.6 g, 10 mmol) was dissolved in toluene (10 mL) at 25° C. NEt$_3$ (2.1 mL, 15 mmol) was added. After 1 hr, the neat cyclopropylacetylene (1.2 mL, 12 mmol) was added to the mixture. The mixture was stirred at 25° C. for 2 hr. The p-methoxybenzyl protected ketimine (3.69 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with Na$_2$SO$_4$ and concentrated in vacuo.

Heptane was added to the mixture slowly. The white solid was collected by filtration, and dried to give the product (95% yield, 99.3% ee).

EXAMPLE 19

Preparation of the DPC961

The p-methoxybenzyl protected DPC 961 (2 mmol) was dissolved in 10% aqueous $CH_3CN$ (10 mL), and ceric ammonium nitrate (4.4 g, 8 mmol) was added. After stirring for 4 hr at 25° C., the reaction was diluted with water and extracted with EtOAc. The combined organic layer was concentrated in vacuo to afford DPC 961 in 80% yield.

EXAMPLE 20

Addition of Cyclopropylacetylene to the Ketimine

Under argon atmosphere, the amino alcohol ligand (1R, 2R)-2-N,N-dimethyl-1-(4-nitrophenyl)-3-O-t-butyldimethylsilylpropane-1-ol (3.54 g, 10 mmol) and $Zn(OTf)_2$ (3.6 g, 10 mmol) was dissolved in toluene (10 mL) at 25° C. $NEt_3$ (2.1 mL, 15 mmol) was added. After 1 hr, the neat cyclopropylacetylene (1.2 mL, 12 mmol) was added to the mixture. The p-methoxybenzyl protected ketimine (3.69 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with $Na_2SO_4$ and concentrated in vacuo. Heptane was added to the mixture slowly. The white solid was collected by filtration, and dried to give the product (72% yield, 99.1% ee).

EXAMPLE 21

Addition of Cyclopropylacetylene to the Ketimine

Under argon atmosphere, the amino alcohol ligand (1R, 2R)-2-N,N-dimethyl-1-(4-nitrophenyl)-3-O-triphenylmethylpropane-1-ol (4.82 g, 10 mmol) and $Zn(OTf)_2$ (3.6 g, 10 mmol) was dissolved in toluene (10 mL) at 25° C. $NEt_3$ (2.1 mL, 15 mmol) was added. After 1 hr, the neat cyclopropylacetylene(1.2 mL, 12 mmol) was added to the mixture. The p-methoxybenzyl protected ketimine (3.69 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with $Na_2SO_4$ and concentrated in vacuo. Heptane was added to the mixture slowly. The white solid was collected by filtration, and dried to give the product (76% yield, 98.0% ee).

EXAMPLE 22

Addition of Cyclopropylacetylene to the Ketimine

Under argon atmosphere, the amino alcohol ligand (1R, 2R)-2-N-methyl-N-benzyl-1-(4-nitrophenyl)-3-O-triphenylmethylpropane-1-ol (5.58 g, 10 mmol) and $Zn(OTf)_2$ (3.6 g, 10 mmol) was dissolved in toluene (10 mL) at 25° C. $NEt_3$ (2.1 mL, 15 mmol) was added. After 1 hr, the neat cyclopropylacetylene (1.2 mL, 12 mmol) was added to the mixture. The p-methoxybenzyl protected ketimine (3.69 g, 10 mmol) was added in one port. The mixture was stirred at 25° C. for 10 hr. The resulting solution was quenched by adding saturated $NH_4Cl$ aqueous solution. The mixture was extracted with EtOAc. The aqueous was saved for the recovery of ligand. The combined organic layers was dried with $Na_2SO_4$ and concentrated in vacuo. Heptane was added to the mixture slowly. The white solid was collected by filtration, and dried to give the product (80% yield, 51.0% ee).

EXAMPLE 23

Addition of Cyclopropylacetylene to the Ketimine

Under argon atmosphere, the amino alcohol ligand (1R, 2R)-2-N-methyl-N-benzyl-1-(4-nitrophenyl)-3-O-triphenylmethylpropane-1-ol (5.58 g, 10 mmol) and $Cu(OTf)_2$ (3.6 g, 10 mmol) was dissolved in toluene (10 mL) at 25° C. $NEt_3$ (2.1 mL, 15 mmol) was added. After 1 hr, the neat cyclopropylacetylene (1.2 mL, 12 mmol) was added to the mixture. The p-methoxybenzyl protected ketimine (3.69 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with $Na_2SO_4$ and concentrated in vacuo. Heptane was added to the mixture slowly. The white solid was collected by filtration, and dried to give the product (68% yield, 98.0% ee).

EXAMPLE 24

Addition of Cyclopropylacetylene to the Ketimine

Under argon atmosphere, the amino alcohol ligand (1R, 2R)-2-N,N-dimethyl-1-(4-nitrophenyl)-3-O-t-butyldimethylsilylpropane-1-ol (354 mg, 1 mmol) and $Zn(OTf)_2$ (0.36 g, 1 mmol) was dissolved in toluene (10 mL) at 25° C. $NEt_3$ (0.21 mL, 1.5 mmol) was added. After 1 hr, the neat cyclopropylacetylene (1.2 mL, 12 mmol) was added to the mixture. The p-methoxybenzyl protected ketimine (3.69 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with $Na_2SO_4$ and concentrated in vacuo. Heptane was added to the mixture slowly. The white solid was collected by filtration, and dried to give the product (75% yield, 98.1% ee).

EXAMPLE 25

Addition of Cyclopropylacetylene to the Ketimine

Under argon atmosphere, the amino alcohol ligand (1R, 2R)-2-N-methyl-N-benzyl-1-(4-nitrophenyl)-3-O-triphenylmethylpropane-1-ol (558 mg, 1 mmol) and $Cu(OTf)_2$ (0.36 g, 1 mmol) was dissolved in toluene (10 mL) at 25° C. $NEt_3$ (0.21 mL, 1.5 mmol) was added. After 1 hr, the neat cyclopropylacetylene (1.2 mL, 12 mmol) was added to the mixture. The p-methoxybenzyl protected ketimine (3.69 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with $Na_2SO_4$ and concentrated in vacuo. Heptane was added to the mixture slowly. The white solid was collected by filtration, and dried to give the product (67% yield, 45% ee).

EXAMPLE 26

Addition of t-butylacetylene to the Ketimine

Under argon atmosphere, the amino alcohol ligand (1R, 2R)-2-N,N-dimethyl-1-(4-nitrophenyl)-3-O-t-butyldimethylsilylpropane-1-ol (3.54 g, 10 mmol) and Zn(OTf)$_2$ (3.6 g, 10 mmol) was dissolved in toluene (10 mL) at 25° C. HNiPr$_2$ (2.0 mL) was added. After 1 hr, the neat t-butylacetylene (1.3 mL, 12 mmol) was added to the mixture. The p-methoxybenzyl protected ketimine (3.69 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with Na$_2$SO$_4$ and concentrated in vacuo. Heptane was added to the mixture slowly. The white solid was collected by filtration, and dried to give the product (45% yield, 96.5% ee).

EXAMPLE 27

Addition of Cyclopropylacetylene to the Ketimine

Under argon atmosphere, the amino alcohol ligand (1R, 2R)-2-N,N-dimethyl-1-(4-nitrophenyl)-3-O-t-butyldimethylsilylpropane-1-ol (3.54 kg, 10 mol) and Zn(OTf)$_2$ (3.6 kg, 10 mol) was dissolved in toluene (10 L) at 25° C. NEt$_3$ (2.0 L, 15 mol) was added. After 1 hr, the neat cyclopropylacetylene (1.2 L, 12 mol) was added to the mixture. The p-methoxybenzyl protected ketimine (3.69 kg, 10 mol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with Na$_2$SO$_4$ and concentrated in vacuo. Heptane was added to the mixture slowly. The white solid was collected by filtration, and dried to give the product (90.9% yield, 99.1% ee).

EXAMPLE 28

Addition of Phenylacetylene to the Ketimine

Under argon atmosphere, the amino alcohol ligand (1R, 2R)-2-N,N-dimethyl-1-(4-nitrophenyl)-3-O-t-butylpropane-1-ol (2.96 g, 10 mmol) and Zn(OTf)$_2$ (3.6 g, 10 mmol) was dissolved in THF (10 mL) at 25° C. NEt$_3$ (2.1 mL, 15 mmol) was added. After 1 hr, the neat phenylacetylene (1.1 mL, 12 mmol) was added to the mixture. The p-methoxybenzyl protected ketimine (3.69 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with Na$_2$SO$_4$ and concentrated in vacuo. Heptane was added to the mixture slowly. The white solid was collected by filtration, and dried to give the product (91% yield, 99.0% ee).

EXAMPLE 29

Addition of Cyclopropylacetylene to the Ketimine

Under argon atmosphere, the amino alcohol ligand (1R, 2R)-2-N,N-dimethyl-1-(4-nitrophenyl)-3-O-t-butyldimethylsilylpropane-1-ol (3.54 g, 10 mmol) and Zn(OTf)$_2$ (3.6 g, 10 mmol) was dissolved in toluene (10 mL) at 25° C. NEt$_3$ (2.1 mL, 15 mmol) was added. After 1 hr, the neat cyclopropylacetylene (1.2 mL, 12 mmol) was added to the mixture. The mixture was stirred at 50° C. for 2 hr and then cooled to 25° C. The p-methoxybenzyl protected ketimine (3.69 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with Na$_2$SO$_4$ and concentrated in vacuo. Heptane was added to the mixture slowly. The white solid was collected by filtration, and dried to give the product (81% yield, 97.1% ee).

EXAMPLE 30

Addition of Cyclopropylacetylene to the Ketimine

Under argon atmosphere, the amino alcohol ligand (1R, 2R)-2-N,N-dimethylamino-1-(4-nitrophenyl)-3-O-t-butyldimethylsilylpropane-1-ol (3.54 g, 10 mmol) and ZnBr$_2$ (2.3 g, 10 mmol) was dissolved in toluene (10 mL) at 25° C. NEt$_3$ (2.1 mL, 15 mmol) was added. After 1 hr, the neat cyclopropylacetylene (1.2 mL, 12 mmol) was added to the mixture. The mixture was stirred at 50° C. for 2 hr and then cooled to 25° C. The p-methoxybenzyl protected ketimine (3.69 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with Na$_2$SO$_4$ and concentrated in vacuo. Heptane was added to the mixture slowly. The white solid was collected by filtration, and dried to give the product (31% yield, 63.1% ee).

EXAMPLE 31

Addition of Cyclopropylacetylene to the Ketimine

Under argon atmosphere, the amino alcohol ligand (1R, 2R)-2-N,N-dimethylamino-1-(4-nitrophenyl)-2-t-butyloxycarbonyl-ethane-1-ol (3.1 g, 10 mmol) and Zn(OTf)$_2$ (3.6 g, 10 mmol) was dissolved in toluene (10 mL) at 25° C. NEt$_3$ (2.1 mL, 15 mmol) was added. After 1 hr, the neat cyclopropylacetylene (1.2 mL, 12 mmol) was added to the mixture. The p-methoxybenzyl protected ketimine (3.69 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with Na$_2$SO$_4$ and concentrated in vacuo. Heptane was added to the mixture slowly. The white solid was collected by filtration, and dried to give the product (95% yield, 99.3% ee).

EXAMPLE 32

Addition of Cyclopropylacetylene to the Ketimine

Under argon atmosphere, the amino alcohol ligand (1R, 2R)-2-N,N-dimethylamino-1-(4-nitrophenyl)-2-hydroxycarbonyl-ethane-1-ol (2.5 g, 10 mmol) and Zn(OTf)$_2$ (3.6 g, 10 mmol) was dissolved in toluene (10 mL) at 25° C. NEt$_3$ (2.1 mL, 15 mmol) was added. After 1 hr, the neat cyclopropylacetylene(1.2 mL, 12 mmol) was added to the mixture. The p-methoxybenzyl protected ketimine (3.69 g, 10 mmol)

was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with $Na_2SO_4$ and concentrated in vacuo. Heptane was added to the mixture slowly. The white solid was collected by filtration, and dried to give the product (95% yield, 90.3% ee).

EXAMPLE 33

Addition of Cyclopropylacetylene to the Ketimine

Under argon atmosphere, the amino alcohol ligand (1R, 2R)-2-N,N-dimethylamino-1-(4-nitrophenyl)-2-methyl-ethane-1-ol (2.3 g, 10 mmol) and $Zn(OTf)_2$ (3.6 g, 10 mmol) was dissolved in toluene (10 mL) at 25° C. $NEt_3$ (2.1 mL, 15 mmol) was added. After 1 hr, the neat cyclopropylacetylene (1.2 mL, 12 mmol) was added to the mixture. The p-methoxybenzyl protected ketimine (3.69 g, 10 mmol) was added in one port. The mixture was stirred at 25° C. for 10 hr. The resulting solution was quenched by adding saturated citric acid aqueous solution. The mixture was extracted with EtOAc. The aqueous was saved for the recovery of ligand. The combined organic layers was dried with $Na_2SO_4$ and concentrated in vacuo. Heptane was added to the mixture slowly. The white solid was collected by filtration, and dried to give the product (95% yield, 60.5% ee).

What is claimed is:

1. A process for synthesizing a chiral compound having a formula of

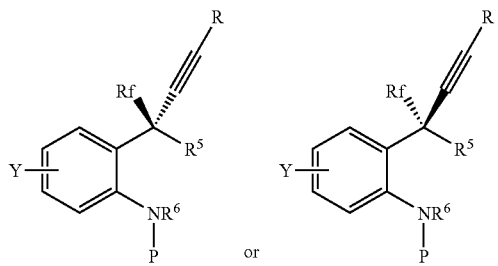

wherein Y is H, mono- or multi-substituted electron-withdrawing group or electron-donating group, and is located at m-, o-, or p-position of the benzene ring;
P is hydrogen or an amino protecting group;
Rf is a fluoro-containing alkyl;
R is a trialkylsilyl, alkyl, cycloalkyl, or aryl group;
$R^6$ is hydrogen and $R^5$ is hydroxy, or $R^5$ and $R^6$ are linked as —HNCO— to form a ring as in

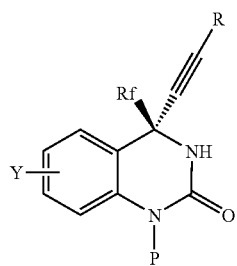

or its enantiomer, comprising the steps of
(a) mixing a chiral ligand (1R,2R)-2-N,N— substituted-1-(substituted-phenyl)-2-$R^3$-substituted-2-aminoethanol or its enantiomer having a formula of

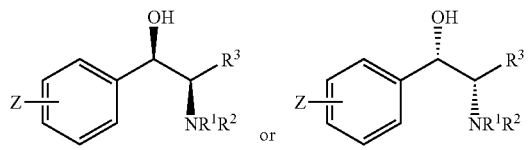

with a terminal alkyne and a Zn(II), Cu(II) or Cu(I) salt in the presence of an organic base in an aprotic solvent to form a mixture,
wherein $R^1$, $R^2$ is an amino protecting group; $R^3$ is an alkyl, alkyl-substituted with an alkyloxy or silyoxy, carboxylic group, carbalkoxy group, hydroxyl methyl, cycloalkyl, aryl, or $CH_2OR^4$, $R^4$ being an oxygen protecting group; Z is H, a mono- or multi-substituted electron-withdrawing group or electron-donating group, and located at m-, o-, or p-position of the benzene ring, and
wherein the terminal alkyne is

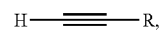

and R is a trialkylsilyl, alkyl, cycloalkyl, or aryl group,
(b) mixing the mixture with a reactant having a formula of

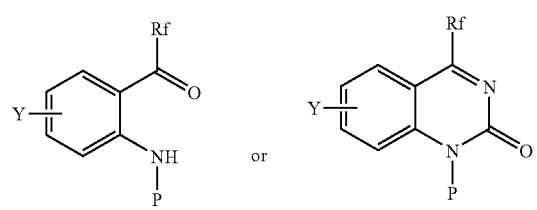

wherein P is hydrogen or an amino protecting group, Rf is a fluoro-containing alkyl, Y is H, a mono- or multi-subsubstituted electron-withdrawing group or electron-donating group and located at m-, o-, or p-positon of the ring, and
(c) isolating and obtaining the chiral compound.

2. The process of claim 1, wherein the chiral ligand (1R, 2R)-2-N,N— substituted-1-(substituted-phenyl)-2-$R^3$-substituted-2-aminoethanol or its enantiomer is (1R,2R)-2-N,N-substitutedamino-1-(substituted-phenyl)-2-substituted-2-aminoethanol having a formula of

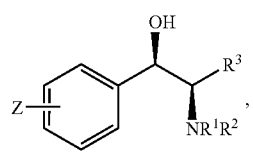

and the reactant is

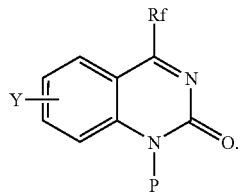

3. The process of claim 2, wherein the chiral ligand is (1R,2R)-2-N,N-substitutedamino-1-(substituted-phenyl)-3-O—R$^4$substituted-propane-1-ol or its enantiomer having a formula of

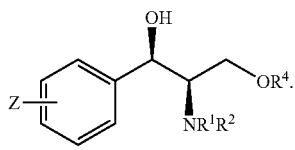

4. The process of claim 1, wherein the chiral ligand is (1R,2R)-2-N,N— substitutedamino-1-(substituted-phenyl)-2-R$^3$-substituted-1-ethanol or its enantiomer having a formula of

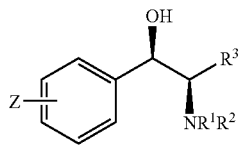

and the reactant is

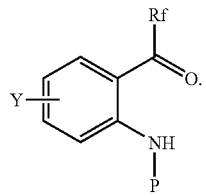

5. The process of claim 1, wherein R$^1$ and R$^2$ is an alkyl, substituted alkyl, benzyl, trialkylsilyl, or substituted benzyl, the substituted group being a phenyl, naphenyl, halo, nitro, hydroxy, $C_1$~$C_3$ hydroxyalkyl, $C_1$~$C_4$ alkyl, or $C_1$~$C_3$ alkoxy, or R$^1$, R$^2$ being —(CH$_2$)$_n$X(CH$_2$)$_m$—, X being CH$_2$, O, or NH; n, m is an integer from 1 to 6;
  P is hydrogen, an alkyl, substituted alkyl, benzyl, trialkylsilyl, or substituted benzyl, the substituted group being a phenyl, naphenyl, halo, nitro, hydroxy;
  R$^4$ is an alkyl, substituted alkyl, benzyl, trialkylsilyl, or substituted benzyl, the substituted group being a phenyl, naphenyl, halo, nitro, hydroxy, $C_1$~$C_3$ hydroxyalkyl, $C_1$~$C_4$ alkyl, $C_1$~$C_3$ alkoxy or CN;
  the electron-withdrawing group is a halogen, NO$_2$, CF$_3$, CH$_3$SO$_2$, CH$_3$CH$_2$SO$_2$, PhCH$_2$OCO, or AcO;
  the electron-donating group is an alkoxy, OH, Me$_2$NCH$_2$CH$_2$O, Et$_2$NCH$_2$CH$_2$O, NH$_2$, or $C_1$~$C_4$ alkyl.

6. The process of claim 1, wherein R$^1$ and R$^2$ is a $C_1$~$C_{20}$ alkyl, $C_1$~$C_{20}$ substituted alkyl, trialkylsilyl, benzyl, or substituted benzyl, the substituted group being a phenyl, naphenyl, halo, nitro, hydroxy, $C_1$~$C_3$ hydroxy alkyl, $C_1$~$C_{20}$ alkyl, or $C_1$~$C_3$ alkoxy, or R$^1$, R$^2$ being —(CH$_2$)$_n$X(CH$_2$)$_m$—, X being CH$_2$, O, or NH;

n, m is an integer from 1 to 6;
  R$^3$ is a $C_1$~$C_{20}$ alkyl, $C_1$~$C_{20}$ alkyl substituted with an alkyloxy or silyoxy, carboxylic group, $C_1$-$C_{20}$ carbalkoxy group, hydroxyl methyl, $C_3$~$C_{20}$ cycloalkyl, aryl, or CH$_2$OR$^4$, R$^4$ being a $C_1$~$C_{20}$ alkyl, $C_1$~$C_{20}$ substituted alkyl, benzyl, or substituted benzyl, the substituted group being a phenyl, naphenyl, halo, nitro, hydroxy, $C_1$~$C_{20}$ hydroxyalkyl, $C_1$~$C_4$ alkyl, $C_1$~$C_3$ alkoxy, or CN;
  Z is H, F, Cl, Br, I, CH$_3$SO$_2$, OH, PhCH$_2$O, AcO, MeO, EtO, Me$_2$NCH$_2$CH$_2$O, Et$_2$NCH$_2$CH$_2$O, PhCH$_2$OCO, t-Bu, i-Pr, NH$_2$, or NO$_2$;
  P is hydrogen, a $C_1$~$C_{20}$ alkyl, $C_1$~$C_{20}$ substituted alkyl, benzyl, trialkylsilyl or substituted benzyl, the substituted group being a phenyl, naphenyl, halo, nitro, hydroxy, $C_1$~$C_3$ hydroxyalkyl, $C_1$~$C_4$ alkyl, $C_1$~$C_3$ alkoxy, or CN;
  Y is H, F, Cl, Br, I, CH$_3$SO$_2$, OH, PhCH$_2$O, AcO, MeO, EtO, Me$_2$NCH$_2$CH$_2$O, Et$_2$NCH$_2$CH$_2$O, PhCH$_2$OCO, t-Bu, i-Pr, NH$_2$, or NO$_2$;
  Rf is a $C_1$~$C_{20}$ fluoro-containing alkyl;
  R is a trialkylsilyl, $C_1$~$C_{20}$ alkyl, $C_3$~$C_{20}$ cycloalkyl, or aryl group.

7. The process of claim 1, wherein R$^1$ and R$^2$ is a $C_1$~$C_4$ alkyl, tri-phenylmethyl, t-butyldimethylsilyl, benzyl unsubstituted or substituted with $C_1$~$C_4$ alkyl, para-methoxy benzyl, pera-nitrobenzyl, para-chlorobenzyl, 2,4-dichlorobenzyl, or 2,4-dimethoxybenzyl, or R$^1$, R$^2$ being —(CH$_2$)$_2$O (CH$_2$)$_2$—, —(CH$_2$)$_2$N(CH$_3$)$_2$—, —(CH$_2$)$_5$—, or —(CH$_2$)$_6$—;
  R$^3$ is a $C_1$~$C_4$ alkyl, $C_1$~$C_4$ alkyl substituted with alkyloxy or silyoxy, carboxylic group, $C_1$~$C_4$ carbalkoxy group, hydroxyl methyl, $C_3$~$C_6$ cycloalkyl , aryl or CH$_2$OR$^4$, R$^4$ being a $C_1$~$C_4$ alkyl, tri-phenyl methyl, t-butyl-dimethylsilyl, benzyl unsubstituted or substituted with $C_1$~$C_4$ alkyl, para-methoxy benzyl, para-nitrobenzyl, para-chlorobenzyl, 2,4-dichlorobenzyl, 2,4-dimethoxybenzyl, or trialkylsilyl groups;
  Z is H, F, Cl, Br, I, CH$_3$SO$_2$, OH, PhCH$_2$O, AcO, MeO, EtO, Me$_2$NCH$_2$CH$_2$O, Et$_2$NCH$_2$CH$_2$O, PhCH$_2$OCO, t-Bu, i-Pr, NH$_2$, or NO$_2$;
  P is hydrogen, a $C_1$~$C_4$ alkyl , tri-phenylmethyl, t-butyldimethylsilyl, benzyl unsubstituted or substituted with $C_1$~$C_4$ alkyl; para-methoxy benzyl, para-nitrobenzyl, para-chlorobenzyl, 2,4-dichlorobenzyl, or 2,4-dimethoxy-benzyl;
  Y is H, Cl, Br, CH$_3$SO$_2$, CH$_3$CH$_2$SO$_2$, NO$_2$, or F;
  Rf is a $C_1$~$C_4$ fluoro-containing alkyl;
  R is a $C_1$~$C_4$ alkyl, $C_3$~$C_6$ cycloalkyl, or aryl group, aryl being a phenyl, naphenyl, furan, thiophene, or pyrrole;
  halogen or halo is a fluoro, chloro, bromo, or iodo.

8. The process of claim 1, wherein stoichiometric ratios are about 0.1-3:0.1-3:1-4:1 of ligand:Zinc salt:the organic base: substrate ketone or ketimine.

9. The process of claim 1, wherein the salt is ZnCl$_2$, ZnBr$_2$, ZnF$_2$, ZnI$_2$, Zn(OTf)$_2$, CuCl$_2$, CuBr$_2$, Cu(OTf)$_2$, CuCl, CuBr, or Cu(OTf).

10. The process of claim 1, wherein the organic base is MeN(iPr)$_2$, HNEt$_2$, N(iPr)$_3$, pyridine, NEt$_3$, piperidine, EtN(iPr)$_2$, or Bu$_3$N.

11. The process of claim 1, wherein reaction temperature is 0-100° C.

12. The process of claim 11, wherein the reaction temperature is 0-50° C.

13. The process of claim 1, wherein the aprotic solvent is THF, dioxane, Et$_2$O, benzene, a mono or multi-alkyl substituted-benzene, DME, toluene, n-hexane, CH$_2$Cl$_2$, cyclohexane, or a mixture thereof.

14. The process of claim 1, further comprising the step of quenching the mixture by adding a proton source to give the chiral compound.

15. The process of claim 1 for asymmetric synthesis of chiral compound of

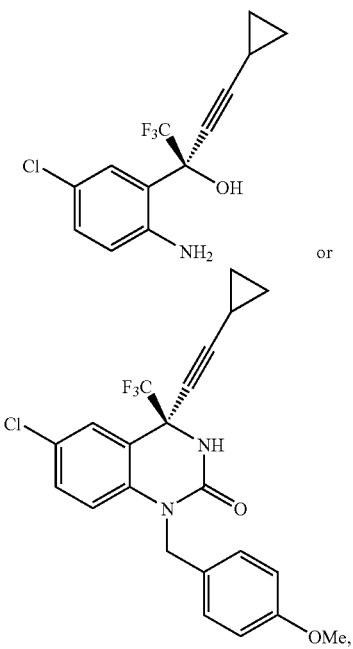

comprising the steps of
(a) mixing 0.1~3 molar equivalent of (1R,2R)-2-N,N-substitutedamino-1-(4-Z-substituted-phenyl)-3-O—R$^4$-substituted propane-1-ol having a formula of

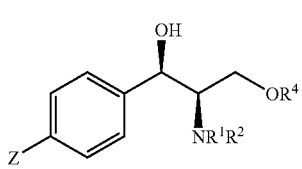

with 0.1~3 molar equivalent of cyclopropylacetylene, 0.1~3 molar equivalent of Zn(II), Cu(I) or Cu(II) salts, and 1~4 molar equivalent of an organic base in organic solvent to form a mixture;
(b) mixing the mixture of step (a) with 1.0 molar equivalent of a reactant having a formula of

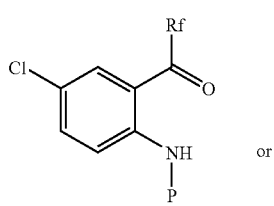

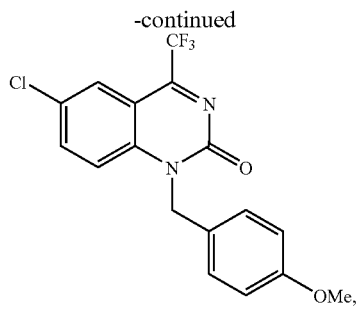

and maintaining resulting reaction mixture at a temperature of between about 0-50° for 1-20 hrs;
(c) quenching by adding a proton source;
(d) obtaining the chiral compound.

16. A compound or its enantiomer having a formula of

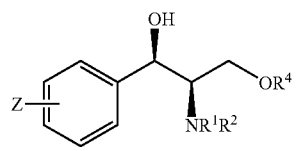

wherein R$^1$, R$^2$ is an amino protecting group;
R$^4$ is an oxygen protecting group;
Z is NO$_2$, CH$_3$SO$_2$, or CH$_3$CH$_2$SO$_2$, and
when Z is NO$_2$ at 4-postion of the phenyl, R$^1$ is N=O, R$^2$ is COCH$_3$, R$^4$ is an alkyl, substituted alkyl, benzyl, substituted benzyl, or trialkylsilyl, or
when Z is NO$_2$ at 4-postion of the phenyl, R$^1$, R$^2$ is CH$_3$, the ligand is (1R,2R)-2-N,N-dimethylamino-1-(4-nitrophenyl)-3-O—R$^4$-1-propanol.

17. The compound of claim 16 having a formula of or its enantiomer

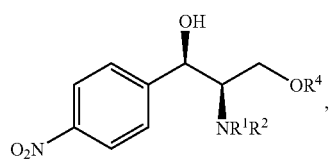

wherein Z is NO$_2$ at 4 position of the phenyl.

18. The compound of claim 16, having a formula of or its enantiomer

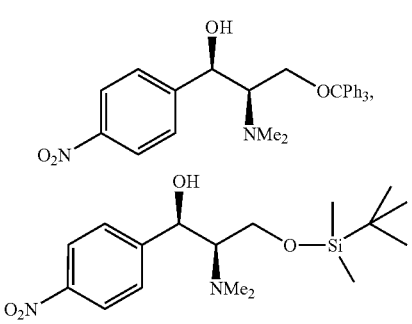

-continued

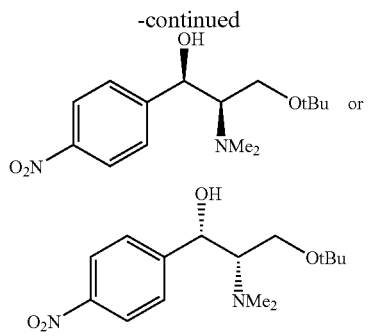

19. The compound of claim 16, wherein $R^1$ and $R^2$ is an alkyl, substituted alkyl, benzyl, trialkylsilyl, or substituted benzyl, the substituted group being a phenyl, naphenyl, halo, nitro, hydroxy, $C_1$~$C_3$ hydroxyalkyl, $C_1$~$C_4$ alkyl, or $C_1$~$C_3$ alkoxy, or $R^1$, $R^2$ being —$(CH_2)_nX(CH_2)_m$—, X being a $CH_2$, O, or NH;

n, m is an integer from 1 to 6;

$R^4$ is an alkyl, substituted alkyl, benzyl, or substituted benzyl, the substituted group being a phenyl, naphenyl, halo, nitro, hydroxy, $C_1$~$C_3$ hydroxy alkyl, alkyl, $C_1$~$C_3$ alkoxy, or CN;

Z is $NO_2$, $CH_3SO_2$, or $CH_3CH_2SO_2$, and when Z is $NO_2$ at 4-postion of the phenyl, $R^1$ is N=O, $R^2$ is $COCH_3$, $R^4$ is only alkyl, substituted alkyl, benzyl, substituted benzyl, or trialkylsilyl, or when Z is $NO_2$ at 4-postion of the phenyl, $R^1$, $R^2$ is $CH_3$, the ligand is (1R,2R)-2-N,N-dimethyl-1-(4-nitrophenyl)-3-O—$R^4$-1-propanol.

20. The compound of claim 16, wherein $R^1$ and $R^2$ is a $C_1$~$C_{20}$ alkyl, $C_1$~$C_{20}$ substituted alkyl, trialkylsilyl, benzyl, or substituted benzyl, the substituted group of alkyl or benzyl being a phenyl, naphenyl, halo, nitro, hydroxy, $C_1$~$C_3$ hydroxyalkyl, $C_1$~$C_4$ alkyl, $C_1$~$C_3$ alkoxy, or CN, or $R^1$, $R^2$ being —$(CH_2)_nX(CH_2)_m$—, X being $CH_2$, O or NH;

n, m is an integer from 1 to 6;

$R^4$ is a $C_1$~$C_{20}$ alkyl, $C_1$~$C_{20}$ substituted alkyl, benzyl, trialkylsilyl, or substituted benzyl, the substituted group being a phenyl, naphenyl, halo, nitro, hydroxy, $C_1$~$C_3$ hydroxyalkyl, $C_1$~$C_4$ alkyl, $C_1$~$C_3$ alkoxy, or CN;

Z is $CH_3SO_2$ or $NO_2$, and when Z is $NO_2$ at 4-postion of the phenyl, $R^1$ is N=O, $R^2$ is $COCH_3$, $R^4$ is an alkyl, substituted alkyl, benzyl, substituted benzyl, or trialkylsilyloxy, or when Z is $NO_2$ at 4-postion of the phenyl, $R^1$, $R^2$ is $CH_3$, the ligand is (1R,2R)-2-N,N-dimethyl-amino-1-(4-nitrophenyl)-3-O—$R^4$-propane-1-ol.

21. The compound of claim 16, wherein $R^1$ and $R^2$ is a $C_1$~$C_4$ alkyl, tri-phenyl methyl, t-butyldimethylsilyl, benzyl unsubstituted or substituted with $C_1$~$C_4$ alkyl, para-methoxy benzyl, para-nitrobenzyl, para-chlorobenzyl, 2,4-dichlorobenzyl, 2,4-dimethoxybenzyl;

$R^4$ is a $C_1$~$C_4$ alkyl, tri-phenyl methyl, t-butyldimethylsilyl, benzyl unsubstituted or substituted with $C_1$~$C_4$ alkyl, para-methoxy benzyl, para-nitrobenzyl, para-chlorobenzyl, 2,4-dichlorobenzyl, or 2,4-dimethoxybenzyl;

Z is $CH_3SO_2$ or $NO_2$, and when Z is $NO_2$ at 4-postion of the phenyl, $R^1$ is N=O, $R^2$ is $COCH_3$, $R^4$ is an alkyl, substituted alkyl, benzyl, substituted benzyl, or trialkylsilyl, or when Z is $NO_2$ at 4-postion of the phenyl, $R^1$, $R^2$ is $CH_3$, the ligand is (1R,2R)-2-N,N-dimethyl-amino-1-(4-nitrophenyl)-3-O—$R^4$-propane-1-ol.

* * * * *